(12) United States Patent
Sung et al.

(10) Patent No.: US 7,582,466 B2
(45) Date of Patent: Sep. 1, 2009

(54) BACILLUS SUBTILIS VAR. CHUNGKOOKJANG PRODUCING HIGH MOLECULAR WEIGHT POLY-GAMMA-GLUTAMIC ACID

(75) Inventors: MoonHee Sung, Daejeon (KR); DaeHeoun Baek, Daejeon (KR); SeungGoo Lee, Daejeon (KR); JaeJun Song, Daejeon (KR); SeungPyo Hong, Daejeon (KR); YoonHo Choi, Suwon-si (KR); SunYoung Shin, Iksan-si (KR); JaeSuk Han, Daegu (KR); Makoto Ashiuchi, Nankoku (KR); Kenji Soda, Kyoto (JP)

(73) Assignee: Bioleaders Corporation (KR)

( * ) Notice: Subject to any disclaimer, the term of this patent is extended or adjusted under 35 U.S.C. 154(b) by 303 days.

(21) Appl. No.: 11/324,675

(22) Filed: Dec. 31, 2005

(65) Prior Publication Data

US 2006/0105446 A1    May 18, 2006

Related U.S. Application Data

(62) Division of application No. 10/204,696, filed as application No. PCT/KR01/01372 on Aug. 11, 2001, now Pat. No. 7,091,010.

(30) Foreign Application Priority Data

Jan. 11, 2001    (KR) .................................. 2001-1481

(51) Int. Cl.
    *C12N 1/20*    (2006.01)

(52) U.S. Cl. ................. 435/252.5; 424/93.46; 435/110; 435/68.1

(58) Field of Classification Search ........................ None
    See application file for complete search history.

(56) References Cited

U.S. PATENT DOCUMENTS

| 4,888,193 | A | 12/1989 | Konno et al. |
| 5,447,732 | A | 9/1995 | Tanimoto et al. |
| 5,948,662 | A | 9/1999 | Kobayashi et al. |
| 6,063,409 | A | 5/2000 | Sato et al. |

FOREIGN PATENT DOCUMENTS

JP    2000-333690 A1    12/2000

*Primary Examiner*—Irene Marx
(74) *Attorney, Agent, or Firm*—Steven J. Hultquist; Kelly K. Reynolds; Intellectual Property/Technology Law (57) ABSTRACT

*Bacillus subtilis* var. *chungkookjang*, accession no. KCTC 0697BP, a salt-resistant *B. subtilis* variant isolated from "*chungkookjang*," a traditional Korean fermented soy bean paste. This *B. subtilis* variant produces poly-gamma-glutamic acid (or poly-gamma-glutamate, γ-PGA), an edible, soluble, anionic, and biodegradable high molecular-weight polymer. *Bacillus subtilis* var. *chungkookjang* produces γ-PGA with a higher molecular weight than other extracellular γ-PGAs derived from general *Bacillus* sp. strains. Accordingly, the γ-PGA produced by *Bacillus subtilis* var. *chungkookjang* can be utilized for the development of high value-added products, such as cosmetics, absorption agents, and biodegradable plastic materials.

3 Claims, 6 Drawing Sheets

BACILLUS SUBTILIS VAR. CHUNGKOOKJANG PRODUCING HIGH MOLECULAR WEIGHT POLY-GAMMA-GLUTAMIC ACID

CROSS-REFERENCE TO RELATED APPLICATIONS

This is a divisional of, and claims priority under 35 USC 120 to, U.S. patent application Ser. No. 10/204,696 filed Aug. 23, 2002 now U.S. Pat. No. 7,091,010 in the names of Moon Hee SUNG, et. al. for "*Bacillus Subtilis* Var. *Chungkookjang* Producing High Molecular Weight Poly-Gamma-Glutamic Acid," which in turn was filed under the provisions of 35 USC 371 based on and claiming the priority of International Patent Application PCT/KR01/01372 filed Aug. 11, 2001, claiming the priority of Korean Patent Application No. 2001-1481 filed Jan. 11, 2001. The disclosure of said U.S. patent application Ser. No. 10/204,696, International Patent Application PCT/KR01/01372 and Korean Patent Application No. 2001-1481 are hereby incorporated herein by reference, in their respective entireties, for all purposes, and the priorities of said International Patent Application PCT/KR01/01372 and Korean Patent Application No. 2001-1481 are hereby expressly claimed.

TECHNICAL FIELD

The present invention relates to the salt-resistant *Bacillus subtilis* var. *chungkookjang*, accession number KCTC 0697 BP, derived from "*chungkookjang*", a traditional Korean fermented soybean food, and to the poly-gamma-glutamic acid (or poly-gamma-glutamate, hereinafter referred to as γ-PGA) produced from said strain, which is an edible, soluble, anionic, and biodegradable polymer. In particular, the present invention relates to a novel *Bacillus subtilis* strain that produces an extracellular γ-PGA from an enzyme complex comprised of (1) D-amino acid aminotransferase EC 2.6.1.21, hereinafter referred to as "D-AAT", which transfers the amino group of D-amino acids into keto acid, (2) glutamate racemase EC 5.1.1.3, hereinafter referred to as "GluRA", and alanine recemase, hereinafter referred to as "AlaRA", which catalyze the creation of isomers from alanine and glutamate, and (3) γ-PGA synthetase and γ-PGA produced from said *Bacillus* sp. strain.

Figure 1:
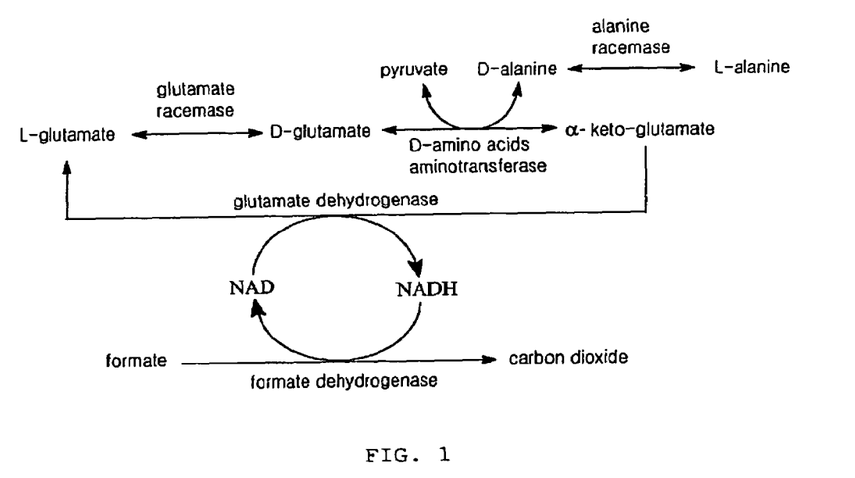
FIG. 1 depicts the biosynthetic pathway of the cell wall and γ-PGA components, which involves various enzymes.

As illustrated in FIG. 1, many enzymes participate in the synthesis of the γ-PGA.

BACKGROUND ART

γ-PGA is a mucous polymer substance consisting of χ-glutamyl conjugated D, L-glutamate and is produced from *Bacillus* sp. strains separated from traditional fermented soybean foods, such as "*chungkookjang*" from Korea, "natto" from Japan, and "kinema" from Nepal. The γ-PGA produced from such *Bacillus* sp. strain is an edible, soluble, anionic, and biodegradable polymer (molecular weight: 100~2,000 kDa), which can be applied as an absorption agent, hygroscopic agent, raw material for cosmetics, and in the manufacture naturally degradable plastic through the synthesis of ester derivatives.

Recently, many studies have been focused on the production and application of γ-PGA, especially in advanced countries. Thus far, researchers have actively attempted to develop materials to replace non-degradable polymers and produce heat-resistant plastic through ester reactions, soluble fibers, and membranes etc. In addition, the physical changes of γ-PGA caused by γ-irradiation have also been studied, along with the development and industrialization of hydrogels using bridge adhesives. For example, the composition of γ-PGA, the effects of Mn ions affecting the production of γ-PGA, uses for soluble polymers degraded by ultrasonication and low soluble plastic through the synthesis of ester derivatives (*Biosci. Biotechnol. Biochem.*, 60(8): 1239-1242, 1996), and the production of γ-PGA in *Bacillus subtilis* and calcium dissolving agents as healthy food for treating osteoporosis (Japanese Laid-open Patent No. Hei. 6-32742) have all been reported. Moreover, the reduction of water contamination based on decreasing the phosphate content in water systems (European Patent No. 838160), a high ratio for making a gel through irradiation, hygienic products, including diapers prepared using a biodegradable adsorptive resin with a water-absorbing property, food, application in the horticultural industry (Japanese Laid-open Patent No. Hei. 10-251402), and it practical use (Japanese Laid-open Patent No. Hei. 7-300522, Japanese Laid-open Patent No. Hei. 6-322358) have also been disclosed. Furthermore, the uses of γ-PGA as a solidified biodegradable fiber or film and film-forming agent through dissolution, precipitation, and drying (Japanese Laid-open Patent No. Hei. 7-138364, and Japanese Laid-open Patent No. Hei. 5-117388), polymers for a drug carrier (Japanese Laid-open Patent No. Hei. 6-92870, Japanese Laid-open Patent No. Hei. 6-256220) have been reported.

Meanwhile, Korean studies, including the efficient production of γ-PGA (Korean Patent Application No. 1997-3404; Korean Patent Application No. 1997-67605) and the improvement of its physical properties have also been performed. While, a Pacific corporation produced γ-PGA from a *Bacillus subtilis* natto strain and used it as a raw material for cosmetics and other practical uses.

DISCLOSURE OF INVENTION

The present inventors have separated a salt-resistant strain, *Bacillus subtilis* var. *chungkookjang* from "*chungkookjang*", a traditional Korean fermented soybean paste, and confirmed that a high level of γ-PGA, an edible, soluble, anionic, and biodegradable polymer can be produced from said *Bacillus subtilis* strain, thereby successfully completing the present invention.

The objective of the present invention is to provide a *Bacillus subtilis* var. *chungkookjang* strain that produces a salt-resistant high molecular-weight γ-PGA.

Another objective of the present invention is to provide a process for preparing a useful recombinant protein at a high ratio in which said *Bacillus subtilis* strain is utilized as the host cell.

Another objective of the present invention is to provide a method for preparing a high molecular-weight γ-PGA in which said *Bacillus subtilis* strain is utilized as the host cell.

Another objective of the present invention is to provide a high molecular-weight γ-PGA produced from said *Bacillus subtilis* strain. Preferably, the present invention provides a γ-PGA with a molecular weight of more than 2,000 kDa.

Another objective of the present invention is to provide cosmetic, food additive, beverage, and pharmaceutical compositions containing said high molecular-weight γ-PGA prepared from said *Bacillus subtilis* strain.

The present invention relates to salt resistant *Bacillus subtilis* var. *chungkookjang*, accession number of KCTC 0697 BP separated from *chungkookjang* traditional fermented soybean food in Korea, and γ-PGA produced from the said *Bacillus subtilis* strain and secreted as an extracellular polymer.

Precisely, the present invention provides a γ-PGA produced from *Bacillus subtilis* var. *chungkookjang*. To support its industrial use, a *Bacillus subtilis* var. *chungkookjang* strain producing γ-PGA on a large scale is separated, the composition of the D- and L-glutamate comprising the γ-PGA produced from the *Bacillus subtilis* strain is examined, and the productivity of the γ-PGA in a culture medium containing L-glutamate is investigated, thereby preparing the fundamentals required for industrial uses.

To obtain microbes producing a biodegradable polymer that can provide the various functions and applications described above, the inventors of the present invention collected *chungkookjang*, which is produced and sold in various regions of Korea, then screened and separated those bacterial strains that had an excellent productive yield of γ-PGA. As a result, the *Bacillus* strain "*Bacillus subtilis chungkookjang*" was identified, which exhibited a higher productivity of γ-PGA than *Bacillus subtilis* natto IFO 3336a and *Bacillus licheniformis* 9945a purified from natto, a traditional Japanese fermented soybean food.

The *Bacillus* sp. strain is obtained from Korean soybean paste called *chungkookjang*, which has been eaten for a long time and thus verified as safe. As such, the γ-PGA with a high molecular weight produced from this *Bacillus* strain can be safely added to food, beverages, health foods, cosmetics, and drugs etc., if properly utilized in the proper quantities.

Hereinafter, the present invention will be more precisely presented.

Separation and Identification of *Bacillus* sp. Strain

The bacterial strain of the present invention, "*Bacillus subtilis chungkookjang*", producing an edible, soluble, anionic, and biodegradable γ-PGA with a high yield and resistant to salts was separated and identified using the following procedure.

To separate high γ-PGA-producing strains, 20 samples of "*chungkookjang*" fermented using rice straw were obtained from various regions in Korea. Each sample was individually suspended in distilled water and heated in a water bath at 60° C. for 20 minutes. Next, small amounts of the heated suspended solutions were smeared onto agar plates (GS) to produce γ-PGA containing 1.5% L-glutamate and cultivated at 37° C. in an incubator for 3 days so as to purify highly mucous bacterial colonies. The separated strains were cultivated through several generations using the same culture medium twice and then the most actively proliferating strain was selected from among the mucous colonies producing γ-PGA. The resulting high γ-PGA-producing strain was identified based on the formation of a milk white colony on an LB agar plate containing a 2% agar and then cultivated through a continuous dilution method at 37° C. for 20 hours so as to purify the prolific strain.

The *Bacillus subtilis chungkookjang* strain in the present invention separated through the above procedure was found to have the following morphological and biological characteristics.

The *Bacillus* sp. strain in the present invention forms a bacterial colony with a milk white color when it is cultivated on an LB agar plate. The strain is a Gram positive bacterium that grows well at a temperature higher than 37° C. under aerobic conditions, yet is retarded at a temperature higher than 55° C. In addition, the strain in the present invention is resistant to salts and can even grow in a 9.0% NaCl concentration, which is higher than the general salt-resistant concentration of *Bacillus subtilis* strains. In addition, the 16S rDNA nucleotide sequence of the strain was also compared with those of conventional *Bacillus* sp. strains. As a result, the *Bacillus* sp. strain in the present invention was confirmed to exhibit a very high homology (99.0%) with *Bacillus subtilis* in its 16S rDNA nucleotide sequence.

The strain in the present invention does not contain any plasmids, which is different from other conventional *Bacillus* sp. strains exploited to produce γ-PGA. Therefore, the present strain can be efficiently utilized as a suitable host for a high expression system of recombinant proteins through gene manipulation. Since the strain separated in the present invention is also an edible and safe microorganism, it can be used as a host cell for expressing vaccines (for example, the antigen of the pig diarrhea virus) and as a fodder additive for treating and preventing diarrhea. As such, the present strain can be applied to the development of oral vaccines.

In addition, the strain separated in the present invention has a negative value in the reduction potential of nitrate salt, is not apt to form spores, and is not easily induced even by Mn ions. Accordingly, based on experimental data, the present strain was classified as *Bacillus subtillus* and named *Bacillus subtilis* var. *chungkookjang*. For the sake of convenience, it was also denoted as *Bacillus* sp. BS-4 and deposited in the Korean Collection for Type Cultures (KCTC; 52, Oun-dong, Yusong-Gu, Taejon) at the Korean Research Institute of Bioscience and Biotechnology (KRIBB), International Deposit Organization, on Nov. 18, 1999 and assigned accession number KCTC 0697 BP.

Analysis of γ-PGA and Measurement of Enzyme Activities

The γ-PGA produced from the above strain was quantitated and the composition of D,L-glutamate in the polymer identified as follows.

"*Bacillus subtilis chungkookjang*" was cultivated and centrifuged. The supernatant containing the γ-PGA was separated, highly concentrated HCl was then added to the supernatant, and the mixture was hydrolyzed at a high temperature. The D,L-glutamate was separated using a stereo-specific HPLC column. To obtain a standard curve, the purified sample of γ-PGA was examined using the same procedure. The substance passing through the column was assayed and quantitated relative to the standard curve of D,L-glutamate, then the corrected value for L-glutamate was added to the initial medium and the separated amount calculated. Finally, the content of the purified γ-PGA was estimated.

To measure the activities of the intracellular enzymes, such as D-AAT, GluRA, and AlaRA, participating directly in the production of the biodegradable γ-PGA, the strain in the present invention was inoculated into 5 ml of an LB broth, cultivated at 37° C. for 10 hours, collected, and lysed in an ultrasonicator. Crude extracts of the enzymes were then collected using a centrifuge. The D-AAT activity was measured by reacting D-alanine and α-keto-glutamate with the crude enzyme extract obtained above in a 0.1 M Tris buffer (Tris-HCl, pH 8.5). Next, the amount of pyruvate generated from the enzymatic reaction in the resulting product was estimated so as to quantitate the activities. In addition, the GluRA activity was calculated by reacting the crude enzyme extract with D-glutamate, α-ketoglutamate, and PLP in 50 mM of a Tris buffer (Tris-HCl, pH 8.5), then the L-glutamate generated from the enzymatic reaction was quantitated using an HPLC column. Thereafter, the AlaRA activity was measured by reacting D-alanine as the substrate and alanine dehydrogenase and quantitating the resulting pyruvate by detecting the absorbance at 340 nm.

BRIEF DESCRIPTION OF DRAWINGS

The above and the other objectives, features, and advantages of the present invention can be more clearly understood from the following drawings, in which.

BEST MODE FOR CARRYING OUT INVENTION

Practical and presently preferred embodiments of the present invention are illustrated in the following Preferred Embodiments.

However, it should be appreciated that those skilled in the art, on consideration of this disclosure, may make modifications and improvements within the scope of the present invention.

Preferred Embodiment 1

Separation and Identification of Bacterial Strains Producing γ-PGA

1. Separation of Microorganism

The traditional fermented soybean paste "*chungkookjang*", fermented using rice straw as the mediator, was collected from various regions in Korea and utilized as the experimental sample. A small amount of each sample was added to sterilized distilled water, suspended, and heated in a water bath at 60° C. for 20 minutes to allow for the formation of endospores. Next, the suspended solution was smeared onto a GS medium plate containing a 2% agar (1.5% L-glutamate, 5.0% sucrose, 0.27% $KH_2PO_4$, 0.42% $Na_2HPO_4$, 0.05% NaCl, 0.05% $MgSO_4$, and 0.05% biotin) and cultivated in an incubator at 37° C. for 3 days. After culturing, those bacterial strains forming mucous bacterial colonies due to the production of γ-PGA were separated.

The separated bacteria were smeared onto general media that do not produce polymers, such as LB, using the continuous dilution method based on the consideration that the culture broths may have been mixed mucous polymers including γ-PGA. Thereafter, the bacterial strain that exhibited the most active cell growth was selectively purified as a γ-PGA-producing strain. The bacterial strain was examined to elucidate its morphological and biochemical properties in a general medium not producing mucous polymers.

To investigate the activity of the enzyme complex composed of various enzymes that participated in the production of polymers from the bacterial strain producing γ-PGA, as obtained above, the separated bacterium was inoculated into 5 ml of an LB broth and cultivated for 10 hours. Next, the cultured medium was centrifuged to recover the bacterial body and sonicated using an ultrasonicator to obtain a crude extract. Thereafter, the resulting extract was used to measure the enzyme activities of D-AAT, GluRA, and AlaRA related to the production of γ-PGA.

2. Morphological and Biochemical Characteristics of Microorganism (1) Growth Characteristics and Morphology of Microorganism The active bacterial strain separated through the above procedure produced an edible, soluble, biodegradable, and anionic γ-PGA in a high yield and produced a highly mucous colony on a GS agar plate as a γ-PGA-producing medium, yet formed a bacterial colony with a milk-white color on an LB agar plate that does not produce mucous polymers. The colonies of the bacterial strain were also found to have sawtoothed boundaries. As to the temperatures affecting bacterial growth, the bacterial strain grew well within a range of 30° C.~55° C., yet it did not proliferate at temperatures higher than 60° C.

The bacterial growth was observed with a microscope using an LB culture broth. As a result, the outer appearance was identified to be Gram positive, short rod-shaped, and similar to that of the comparative *Bacillus subtilis* strains (not depicted). Precisely, the bacterial strain was Gram positive and sized within a range of about 0.7~0.8×2.0~3.0 μm. In contrast, another comparative strain, *Bacillus licheniformis*, has a thin snail and thread shape in the exponential phase, as distinct from the strain separated in the present invention.

(2) Resistance to Sodium Chloride

Figure 2:
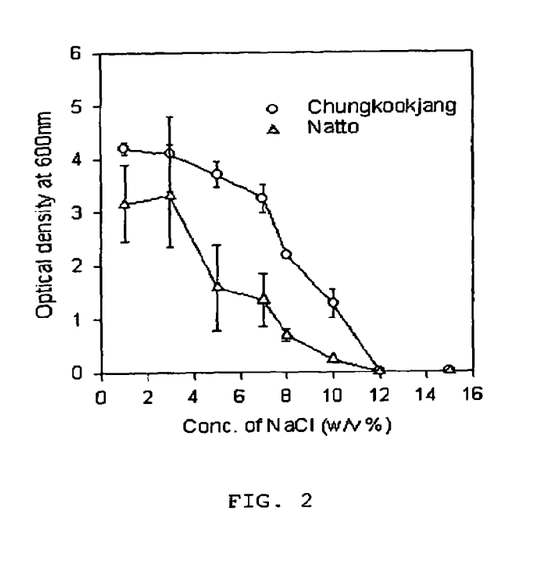
FIG. 2 presents a comparison of the sodium chloride resistance exhibited by *Bacillus subtilis chungkookjang* (the present invention) and *Bacillus subtilis* natto.

The strain in the present invention and the *Bacillus subtilis* natto strain were cultivated in an LB broth containing various concentrations of NaCl for 24 hours, then the bacterial growth was measured by detecting the absorbance at 660 nm (See FIG. 2). As illustrated in FIG. 2, the survival ratio of the bacterial strain (the present invention) was about 2-fold that of *Bacillus subtilis* natto as regards the range of concentrations (12%). That is to say, the bacterial strain in the present invention was confirmed to be resistant to NaCl.

(3) Characteristics of Plasmids in Strain

Figure 3:
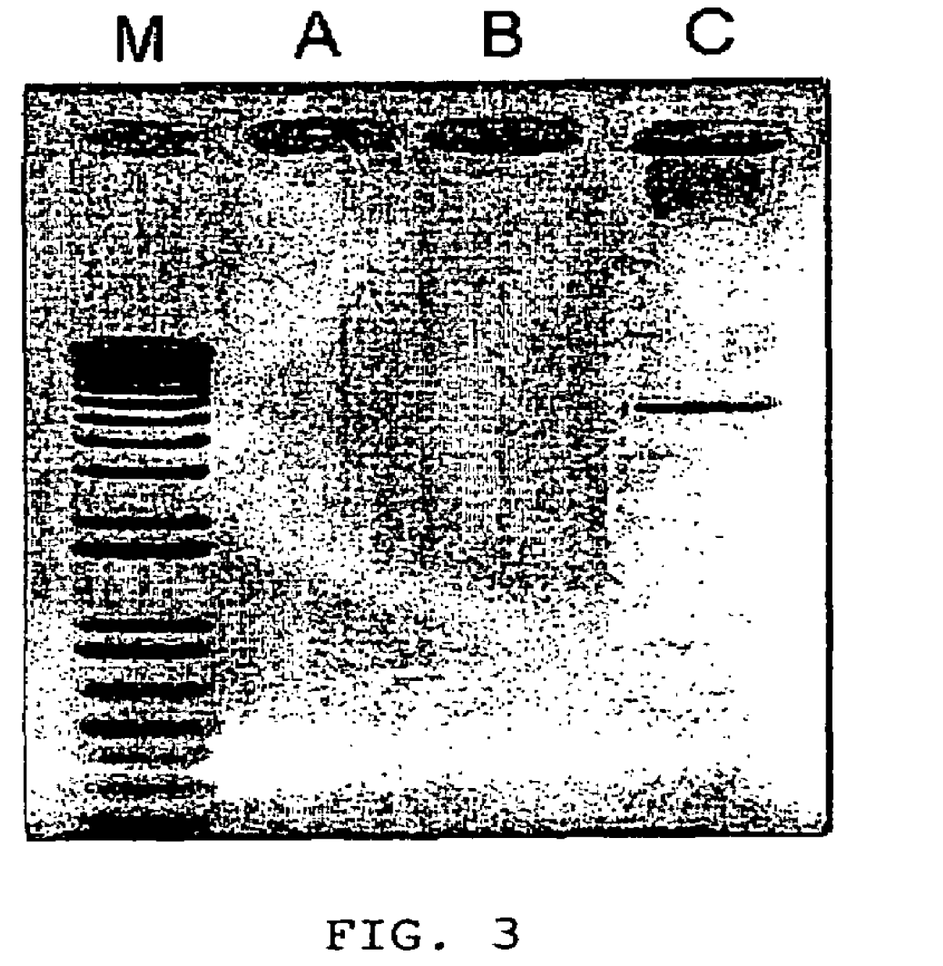
FIG. 3 is a gel electrophoresis depiction of the existence of plasmids in *Bacillus subtilis chungkookjang* (the present invention) and other comparative strains.

The bacterial strain in the present invention, *Bacillus subtilis* 168, and *Bacillus subtilis* natto IFO 3336 were all used to elucidate whether or not they included any plasmids (See FIG. 3). In FIG. 3, lane M denotes a 1 kb ladder; lane A, *Bacillus subtilis* 168; lane B, the strain in the present invention; and lane C, *Bacillus subtilis* natto IFO 3336.

As illustrated in FIG. 3, the strain in the present invention was found not to contain any plasmids even though it can produce γ-PGA, which was different from the *Bacillus subtilis* natto IFO 3336 strain. Interestingly, this result also exhibited the same characteristic as *Bacillus subtilis* 168, which does not produce γ-PGA.

Accordingly, as demonstrated, since the present strain does not contain any plasmids, it can be efficiently utilized as a suitable host for a high expression system (secretion or production) of recombinant proteins through gene manipulation.

(4) Characteristics of Spore Formation

The present strain was inoculated into an LB broth containing 2 mM of $CoSO_4$, cultivated at 37° C. for 4 days, and then observed by staining spores (not depicted). As a result, the bacterial strain separated in the cerrent invention was confirmed to have a much lower activity as regards spore formation, when compared with *Bacillus subtilis* natto, which produces γ-PGA in a similar manner.

(5) Other Biochemical Characteristics

The present strain was investigated to reveal its biochemical properties using API50CHB and API20E kits.

Consequently, *Bacillus subtilis* var. *chungkookjang* (the present invention) was identified as Gram positive, based on reducing activity of nitrate salts and no production of indoles. Also, it degraded gelatin and starch and produced β-glucosidase, β-galactosidase, and oxidase. In addition, it could produce urease and grow under both aerobic and anaerobic conditions. Furthermore, it was found to use glycerol, galactose, glucose, sucrose, maltose, and starch.

The morphological and biochemical properties of the microbes selected in accordance with the present invention were described precisely in Table 1.

(6) Analysis of Nucleotide Sequences

To more accurately identify the strain obtained in the present invention, its 16S rDNA gene was analyzed to determine its nucleotide sequence.

Figure 4:
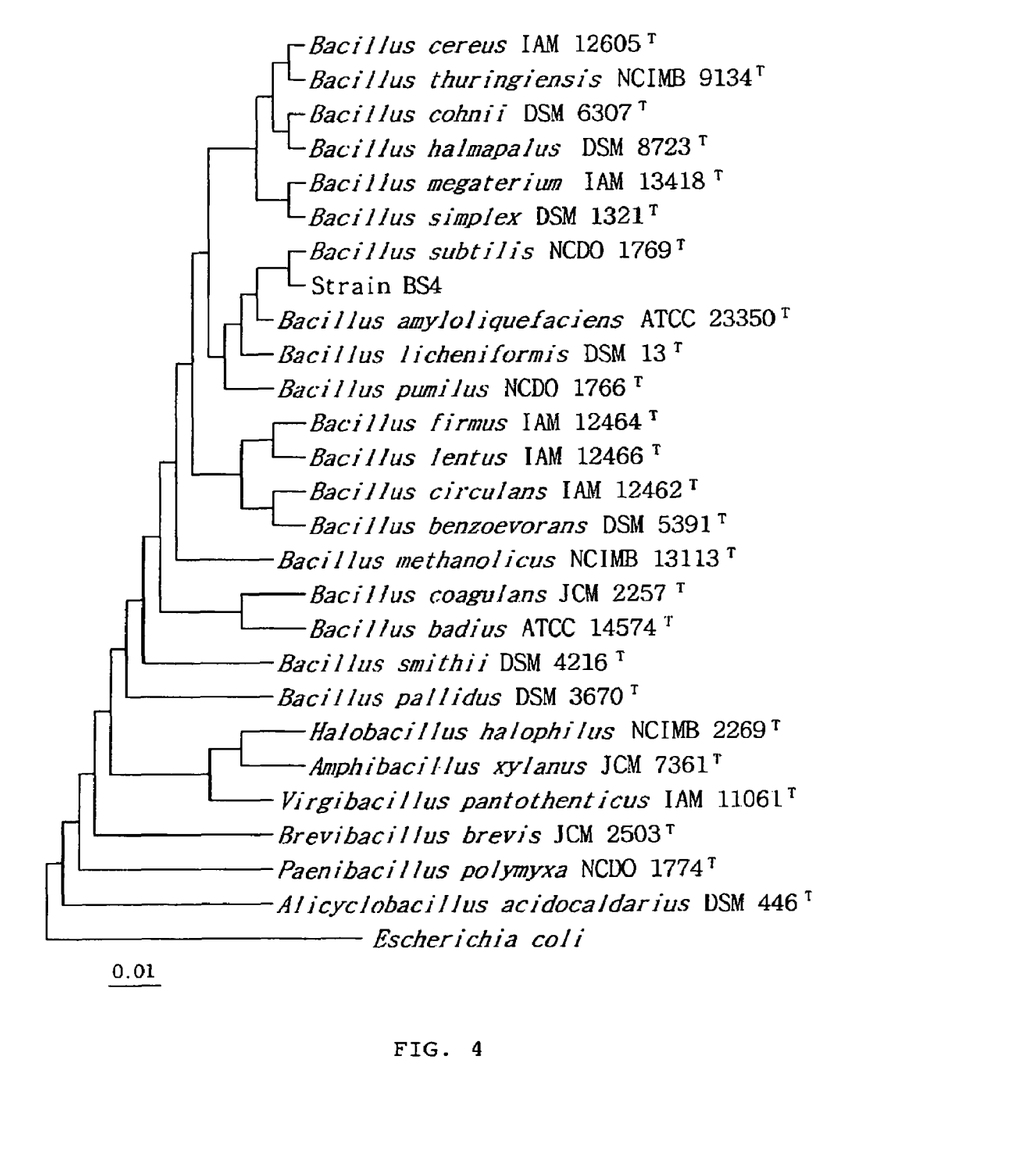
FIG. 4 shows the genealogy of *Bacillus subtilis chungkookjang* (the present invention).

In addition, the N-terminal primer of SEQ NO. 1 (5'-AGAGTTTGATCCTGGCTCAG-3') and C-terminal primer of SEQ NO. 2 (5'-AGAAAGGAGGTGATCCAGCC-3') were used to amplify the 16S rDNA gene using a PCR, then the resulting genes were cloned into the plasmid vector pT7Blue to obtain the total nucleotide sequence. The 16S rDNA nucleotide sequence of the selected microbe was then compared with the 16S rDNA nucleotide sequences of various microbes reported previously to observe their homologies. As a result, the present strain was confirmed to have a 99.0% homology with *Bacillus subtilis* and be situated in the same lineage, as illustrated in FIG. 4.

(7) Identification of Separated Strain

The *Bacillus* sp. strain separated in the present invention was not found to contain any plasmids in spite of its high homology, as described above, which is quite different from conventional *Bacillus* sp. strains producing γ-PGA. This feature means that the separated strain can be efficiently utilized as a suitable host for a high expression system in which recombinant proteins are manufactured through gene manipulation. In addition, as distinct from typical *Bacillus* sp. strains, the separated strain was found to be negative as regards the reduction power of nitrate salts, not apt to form spores, and not easily induced by Mn ions.

The characteristics of the bacterial strain itself and the γ-PGA produced by this strain, as outlined in the preferred embodiment section, helped the strain to be classified as a new *Bacillus subtilis* species. The *Bacillus* sp. strain in the present invention was named *Bacillus subtilis* var. *chungkookjang* and, for the sake of convenience, was denoted as *Bacillus* sp. BS-4 when it was deposited in the Korean Collection for Type Cultures (KCTC; 52, oun-dong, Yusong-Gu, Taejon) at the Korean Research Institute of Bioscience and Biotechnology (KRIBB), International Deposit Organization, on Nov. 18, 1999 and assigned accession number KCTC 0697 BP.

TABLE 1

| characteristics | *Bacillus subtilis* strain of present invention |
|---|---|
| Gram staining | positive |
| shape and size | Rod |
|  | 0.7~0.8 × 2.0~3.0 μm |
| spore formation | weak (not well formed) |
| resistant spore formation | column shape, situated at center of cell |
| growth temperature | 30~55° C. |
| growth at pH 5.7 | Positive |
| growth in 10% NaCl | Positive |
| growth under aerobic conditions | Positive |
| Growth under anaerobic conditions | Positive |
| Movement | positive |
| Voges-Proskauser experiment | positive |
| nitrate salt reduction | negative |
| indole formation | negative |
| oxidase production | positive |
| catalase production | positive |
| urease production | positive |
| β-galactosidase production | positive |
| gelatinase production | positive |
| β-glucosidase production | positive |
| tryptophanase production | negative |
| starch degradation | positive |
| casein degradation | positive |
| citric acid application | positive |
| acid generation from glucose | positive |
| acid generation from glycerol | positive |
| acid generation from galactose | positive |
| acid generation from glucose | positive |
| acid generation from sucrose | positive |
| acid generation from maltose | positive |

Preferred Embodiment 2

Production of γ-PGA

The strain in the present invention was inoculated into a culture broth for the production of γ-PGA and cultivated at 37° for 72 hours. Next, 2 N of a sulfuric acid solution was added, the pH adjusted to 3.0, then experimental samples containing γ-PGA collected. The above samples were left at 4° C. for 10 hours and the polysaccharides within the fermented solution removed. At this point, ethanol was added to create a 2-fold volume and then mixed. The mixed solution was left at 4° C. for 10 hours and centrifuged to obtain the γ-PGA precipitate. The precipitate was then mixed with distilled water, dissolved, reacted again with protease reaching 100 μg/ml and left at 37° C. in an incubator for 6 hours so as to decompose the extracellular proteins in the γ-PGA sample. Next, the resulting solution was dialysed using a sufficient amount of distilled water and the separated glutamate removed. Thereafter, the remaining mixture was concentrated to collect pure γ-PGA, which was then hydrolyzed with acids. Finally, the composition and productive yield of D, L-glutamate were estimated.

The productive yield of γ-PGA with the present strain and comparative strains is demonstrated in Table 2. In a culture broth, the strain in the present invention yielded 16 g/L, while *Bacillus subtilis* natto IFO 3336a and *Bacillus licheniformis* ATCC 9945a separated from natto only yielded 10 g/L and 9 g/L respectively. To compare the productive yields of γ-PGA in solid culture media, a culture medium containing a 2% agar was used to prepare the culture plate, then the bacteria were inoculated, cultivated at 37° C. for 3 days, the γ-PGA purified using the same procedure as above, and the difference in the productive yields compared between the present strain and comparative strains. As a result, the strain in the present invention produced 12 mg per culture plate, *Bacillus subtilis* natto IFO 3336a produced 8 mg per culture plate, and *Bacillus licheniformis* ATCC 9945a produced 6 mg per culture plate. Therefore, the productivity of the present strain was confirmed to be 2-fold that of the comparative strains. In addition, as depicted in the gel pattern in FIG. 5, the amount of γ-PGA produced per 0.3 mg of bacterial weight was also compared. Consequently, the present strain was verified to produce a much larger amount of γ-PGA than the conventional γ-PGA-producing strain, *Bacillus subtilis* natto IFO 3336a.

Preferred Embodiment 3

Examination of Stero-Specificity in γ-PGA and D, L-glutamate

The productive yield of γ-PGA produced by the strain in the present invention was calculated and the composition of D-, L-glutamate in the γ-PGA investigated.

To measure the ratio of D-, L-glutamate, that is the monomer composition in the high molecular-weight γ-PGA, the separated strain was cultivated at 150 rpm and 37° C. in an incubator for 72 hours using a 500 ml triangle flask containing a GS culture medium. Then, the γ-PGA sample, purified through the same procedure as described above, was added with 6 N of HCl, de-aerated, and hydrolyzed at 105° C. for 10 hours.

To analyze the composition of amino acids in the above hydrolyzed product, a concentration gradient of organic solvents, such as a 50 mM phosphate buffer containing 5% methanol (pH 7.0) and methanol, was utilized to perform an HPLC column (RexchromeS5-100-ODS, Regis Chem. Inc., 4.6 mm×25 cm×5 m, U.S.A.). Next, to separate the stereoisomer, o-pthaldialdehyde (OPA) was used to turn the amino terminus of D, L-glutamate into derivatives, then the D, L-glutamate in the γ-PGA was quantitated based on a standard curve for D, L-glutamate using a fluorescence detector at 452 nm (quenching) and 342 nm (luminescence).

The results of the D, L-glutamate content, the monomer composition of the γ-PGA produced above, are illustrated in Table 2. In detail, the D/L-glutamate ratio in the γ-PGA produced from the strain in the present invention was about 40/60, while in the comparative strains the D/L-glutamate ratio was 50/50 for both *Bacillus subtilis* natto IFO 3336a and *Bacillus licheniformis* ATCC 9945a. As such, the present strain was found to have a distinct monomer composition.

(1) Quantitation of Enzyme Activities in Production of γ-PGA

To measure the activity of the enzymes participating in the production of γ-PGA in the present stain, the strain was cultivated at 37° C. in an incubator using an LB broth, which does not produce mucous polymers, and centrifuged. Then, a crude enzyme extract was prepared to calculate the enzymatic activity through the procedure described above.

The D-AAT activity was measured by reacting D-alanine, α-keto-glutamate, and the crude enzyme extract in a 0.1 M Tris buffer (Tris-HCl, pH 8.5) (Berntsson S, *Anal. Chem.*, 27: 1659-1660, 1955). Then, the GluRA activity was calculated by reacting the crude enzyme extract, D-glutamate, α-ketoglutamate, and PLP in a 50 mM Tris buffer (Tris-HCl, pH 8.5), then the L-glutamate generated from the enzymatic reaction was quantitated using an HPLC column. Thereafter, the alanine racemase activity was measured by reacting L-alanine generated from D-alanine as the substrate and alanine dehydrogenase and quantitating the resulting pyruvate by detecting the absorbance (*Biochemistry*, 25: 3261-3267, 1986). The protein content was calculated using the Bradford method (Bradford, M., *Anal. Biochem.*, 72: 248-254, 1976).

After the present strain was cultivated in a triangular flask, the volume and molecular weight of the γ-PGA, D,L-glutamate ratio, and enzymatic activities of D-AAT, GluRA, and AlaRA are all presented in Tables 2 and 3. To compare the γ-PGA properties, *Bacillus subtilis* and *Bacillus licheniformis* separated from Japanese natto and known to produce γ-PGA were utilized to analyze the yield of γ-PGA and the enzymatic activities.

Figure 6:
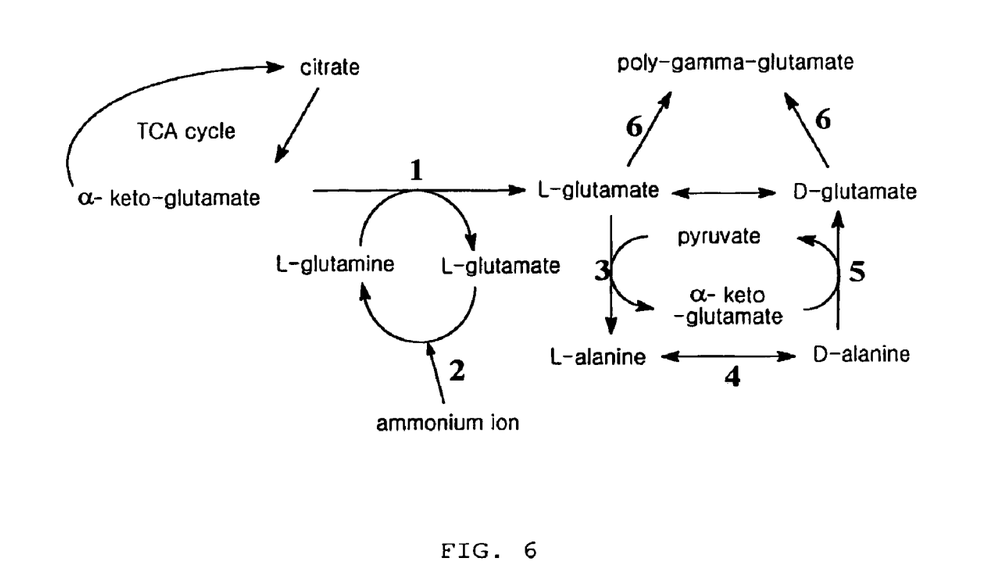
FIG. 6 depicts the hypothetical biosynthetic pathway of the γ-PGA produced from *Bacillus subtilis chungkookjang* (the present invention).

As a result, the strain separated in the present invention was confirmed to synthesize D-Ala and D-Glu, which are essential for cell proliferation, and produce γ-PGA based on AlaRA and GluRA activities. In addition, it is proposed that, since the D-AAT activity in the present strain was found to be 3 times higher than that in *Bacillus subtilis* natto and *Bacillus licheniformis*, this could be exploited for the high production of D-Glu from D-Ala as a direct pathway for the production of γ-PGA. As illustrated in Tables 2 and 3 and FIG. 1, *Bacillus subtilis* natto and *Bacillus licheniformis* would appear to have a synthetic pathway essential for cell proliferation and the synthesis of γ-PGA by high GluRA activity, whereas the present strain indicated a different pathway for the synthesis of amino acids (See FIG. 6). In FIG. 6, lane 1 denotes glutamine: 2-oxoglutarate aminotransferase; lane 2, glutamate synthase; lane 3, L-glutamate: pyruvate aminotransferase; lane 4, alanine racemase; lane 5, D-amino acid aminotransferase; lane 6, γ-PGA synthase; lane TCA, tricarboxylate circuit.

This means that in the case of the *Bacillus subtilis* natto strain, the D-glutamate exploited in the synthesis of γ-PGA was produced from L-glutamate by intracellular glutamate racemase. In contrast, in the case of the *Bacillus subtilis* strain separated in the present invention, the D-glutamate was produced from L-glutamate based on the activity of alanine racemase and D-amino acid aminotransferase.

TABLE 2

Comparison of productivity by strain in present invention and comparative strains

| Strain | γ-PGA (g/L) | D,L-glutamate (D/L ratio) |
|---|---|---|
| *Bacillus subtilis* var. *chungkookjang* of the present invention | 16 | 40/60 |
| *Bacillus subtilis* natto (IFO 3336a) | 10 | 50/50 |
| *Bacillus licheniformis* (ATCC 9945a) | 9 | 50/50 |

TABLE 3

Comparison of enzyme activities related to production of γ-PGA by strain in present invention and comparative strains

| | enzyme activity (units/mg protein) | | |
|---|---|---|---|
| Strain | D-AAT | GluRA | AlaRA |
| *Bacillus subtilis* var. *Chungkookjang* of the present invention | 0.503 | 0.0109 | 0.153 |

TABLE 3-continued

Comparison of enzyme activities related to production of γ-PGA by strain in present invention and comparative strains

| Strain | enzyme activity (units/mg protein) | | |
|---|---|---|---|
| | D-AAT | GluRA | AlaRA |
| Bacillus subtilis natto (IFO 3336a) | 0.165 | 0.0540 | 0.108 |
| Bacillus licheniformis (ATCC 9945a) | 0.187 | 0.0521 | 0.099 |

Preferred Embodiment 4

Comparison of Molecular Weights for γ-PGA (1) Comparison of Molecular Weight Using Gel Electrophoresis A concentration gradient SDS-polyacrylamide gel electrophoresis was performed to compare the molecular weights of the γ-PGA produced from *Bacillus subtilis* var. *chungkookjang* (the present invention), *Bacillus subtilis* 168 a standard *Bacillus* sp. strain, and the comparative strain *Bacillus subtilis* natto IFO 3336.

Figure 5:
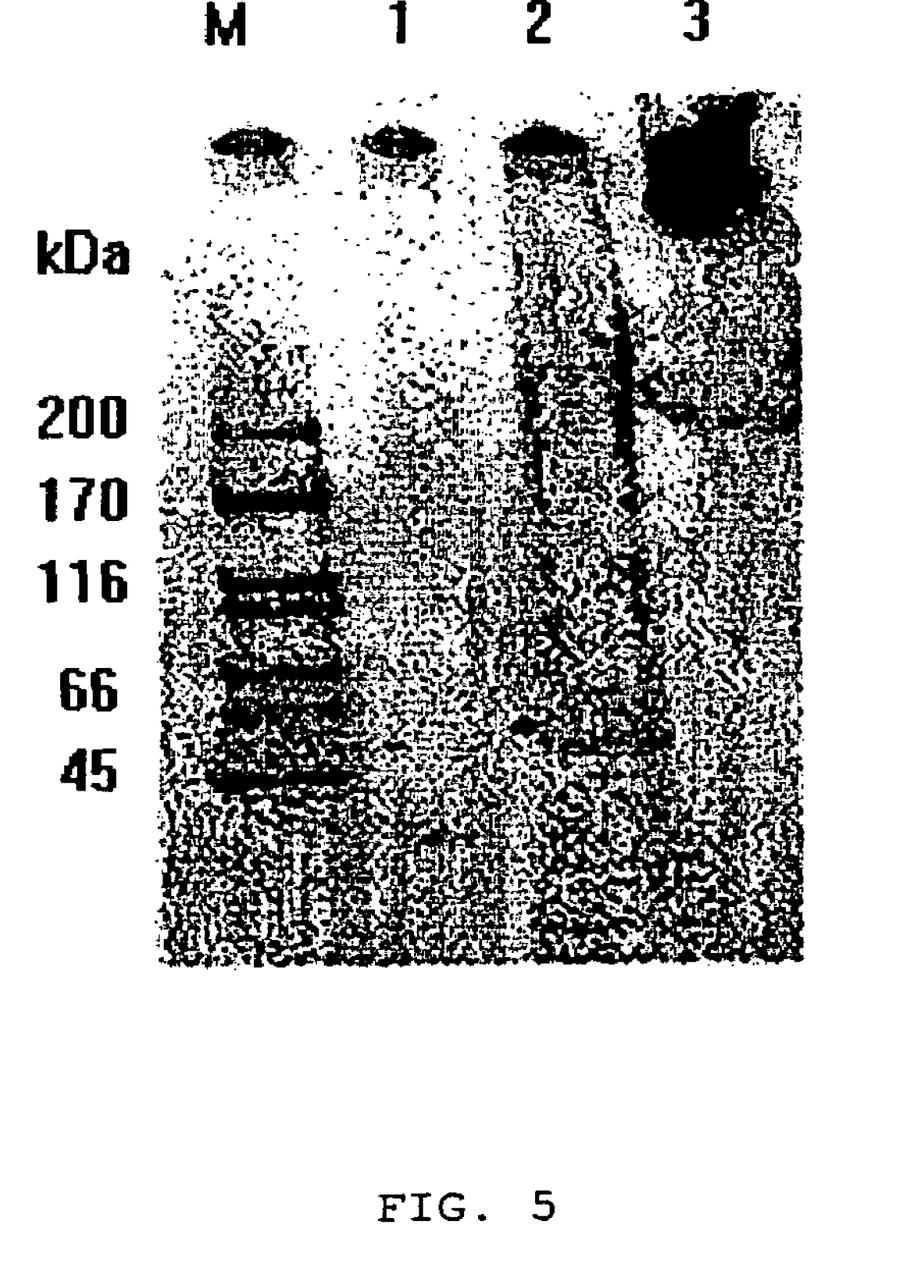
FIG. 5 shows the concentration gradient of SDS-polyacrylamide gel electrophoresis, depicting a comparison of the concentration of γ-PGA produced from *Bacillus subtilis chungkookjang* (the present invention) with that produced by other comparative strains.

The γ-PGA produced from each strain was purified according to the procedure described in the preferred embodiment 2, and made into a solution of about 200 μg/ml. Then, 80 μl of the γ-PGA solution was mixed with 20 μl of a 5× buffer and analyzed by SDS-PAGE using a 5~20% concentration gradient. After completing the electrophoresis, a Comassie reagent and methylene blue were utilized to stain the standard proteins and γ-PGA (See FIG. 5). In FIG. 5, lane M denotes the standard protein; lane 1, *Bacillus subtilis* 168; lane 2, *Bacillus subtilis* natto IFO 3336; and lane 3, the strain in the present invention.

As illustrated in FIG. 5, *Bacillus subtilis chungkookjang* (the present invention) was found to produce γ-PGA with a much higher molecular weight than *Bacillus subtilis* natto, which produced a molecular weight of about 1,000~2,000 kDa.

(2) Estimation of Molecular Weight Using Gel Permeation Chromatography (GPC)

The present strain was cultivated on a GS solid medium for 5 days and the γ-PGA purified using the above procedure. Then, the molecular weight was analyzed by performing gel permeation chromatography (Asahipak GS-620H positive Tosoh TSK gel).

The gel permeation chromatography was accomplished in a column oven at 25° C. using a 50 mM solvent of saline and acetonitrile in a ratio of 4:1 at a flowing velocity of 0.7 ml per minute. Polyethylene oxide was used as the standard substance, and the molecular weight of the γ-PGA was measured using a refraction index detector.

Figure 7:
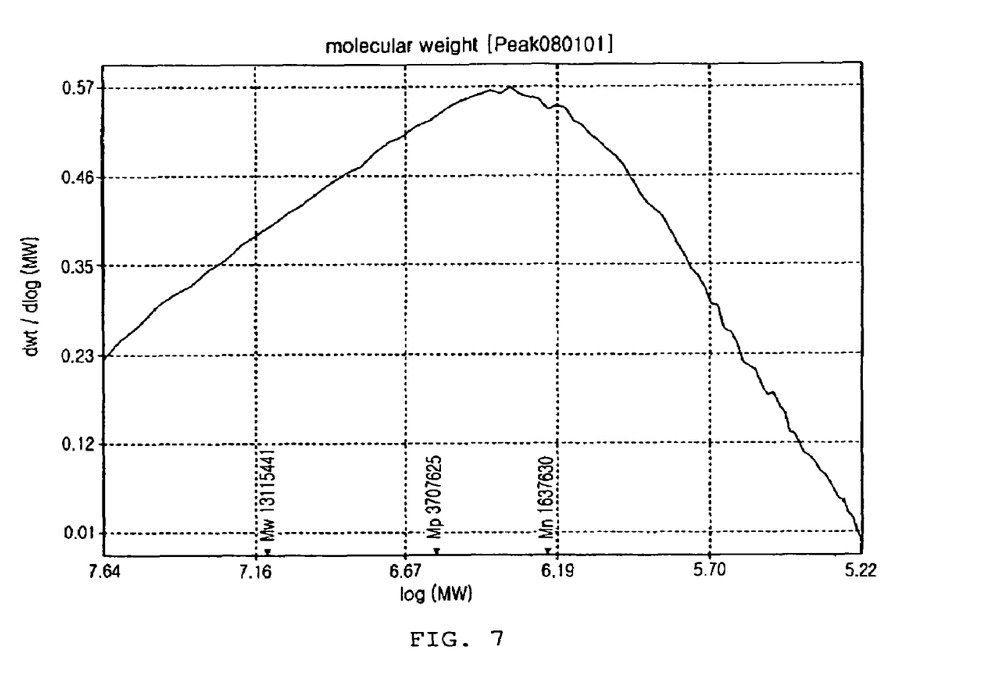
FIG. 7 shows the γ-PGA produced from *Bacillus subtilis chungkookjang* (the present invention) based on gel permeation chromatography.

The experimental results of the chromatography are depicted in FIG. 7. Consequently, the present strain was identified to produce γ-PGA with an average molecular weight of about 13,000,000 and distribution of about 8.0.

Therefore, the γ-PGA produced from the present strain was confirmed to have a much higher molecular weight than that produced from other strains, thereby enabling it to be effectively utilized in the preparation of hydrogels.

Preferred Embodiment 5

Examination of Degradation in γ-PGA of *Bacillus subtilis Chungkookjang*

In the present strain, variations in the molecular weight of the γ-PGA were traced during the culture period by applying GPC.

As such, the present strain was cultivated on a GS solid medium. After 1, 3, and 5 days, the γ-PGA was purified according to the above procedure. Thereafter, the molecular weight and its distribution were investigated by applying GPC (See FIG. 4).

TABLE 4

| culture period (days) | average Mw | Mw distribution |
|---|---|---|
| 1 | $1.204 \times 10^4$ | 7.9 |
| 3 | $1.197 \times 10^4$ | 7.8 |
| 5 | $1.311 \times 10^4$ | 8.0 |

As demonstrated in Table 4, there was no change in the average molecular weight of the synthesized γ-PGA (in the present invention) or its distribution over time. Therefore, the γ-PGA of *Bacillus subtilis chungkookjang* (the present invention) was determined to undergo no or minimal degradation activity.

INDUSTRIAL APPLICABILITY

As demonstrated and confirmed above, the present invention is related to *Bacillus subtilis* var. *chungkookjang*, accession number KCTC 0697 BP, which is derived from a traditional Korean fermented soybean food "*chungkookjang*", resistant to salt, and produces an γ-PGA that is an edible, soluble, anionic, and biodegradable polymer.

*Bacillus subtilis* var. *chungkookjang* (the present invention) was confirmed as producing a higher molecular-weight γ-PGA as well as an outstanding productive yield compared with other extracellular γ-PGAs derived from general *Bacillus* sp. strains. Accordingly, the γ-PGA from the Bacillus subtilis strain in the present invention can be effectively utilized to develop commercial products, such as cosmetic substances, adsorption agents, and biodegradable plastic substances etc., by synthesizing and chemically treating derivatives of the γ-PGA.

What is claimed is:

1. A biologically pure culture of the strain *Bacillus subtilis* var. *chungkookjang* KCTC 0697BP, which produces γ-polyglutamic acid (γ-PGA) as a biodegradable polymer, is resistant to salt, hardly forms spores, does not contain any plasmids, and is obtained from the fermented soybean paste, *chungkookjang*.

2. The biologically pure culture of claim 1, wherein the strain is resistant to the reduction power of nitrate salt.

3. The biologically pure culture of claim 1, wherein the strain produces γ-PGA having an average molecular weight of about 13,000,000 kDa.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial
<220> FEATURE:
<223> OTHER INFORMATION: single stranded oligonucleotide primer

<400> SEQUENCE: 1
agagtttgat cctggctcag                                       20

<210> SEQ ID NO 2
<211> LENGTH: 20
<212> TYPE: DNA
<213> ORGANISM: Artificial
<220> FEATURE:
<223> OTHER INFORMATION: single stranded oligonucleotide primer

<400> SEQUENCE: 2
agaaaggagg tgatccagcc                                       20